(12) United States Patent
Shibutani et al.

(10) Patent No.: US 6,214,294 B1
(45) Date of Patent: Apr. 10, 2001

(54) STIRRING DEVICE AND AUTOMATIC ANALYZER INCORPORATING THE STIRRING DEVICE

(75) Inventors: Hitoshi Shibutani; Kazuyoshi Ikeda, both of Otawara; Kyuji Rokugawa, Tochigi-ken, all of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/136,517

(22) Filed: Aug. 19, 1998

(30) Foreign Application Priority Data

Aug. 20, 1997 (JP) .................................................. 9-223204

(51) Int. Cl.[7] ............................... B01L 3/00; B01F 11/00
(52) U.S. Cl. ........................... 422/99; 366/108; 366/117; 366/127
(58) Field of Search .............................. 422/99, 224, 225, 422/63, 64; 366/108, 116, 117, 118, 127

(56) References Cited

U.S. PATENT DOCUMENTS

| 3,591,862 | * | 7/1971 | Winston ................................ 310/322 |
| 3,770,248 | * | 11/1973 | Cahoon et al. ....................... 366/117 |
| 3,774,317 | * | 11/1973 | Balamuth et al. .................... 434/202 |
| 4,612,291 | * | 9/1986 | Dawes ................................... 436/174 |
| 5,413,770 | * | 5/1995 | Sakaguchi et al. .................. 422/225 |
| 5,449,493 | | 9/1995 | Rokugawa et al. . |

* cited by examiner

*Primary Examiner*—Jan Ludlow
*Assistant Examiner*—Dwayne K Handy
(74) *Attorney, Agent, or Firm*—Oblon, Spivak, McClelland, Maier & Neustadt, P.C.

(57) ABSTRACT

A stirring device has an actuator like a plate, a cover shaped like a rectangular box and covering the actuator, a blade designed to be vibrated by the actuator, and a connecting device connecting the blade to the actuator, positioning an axis of vibration amplitude of the blade substantially in one side of the cover.

16 Claims, 6 Drawing Sheets

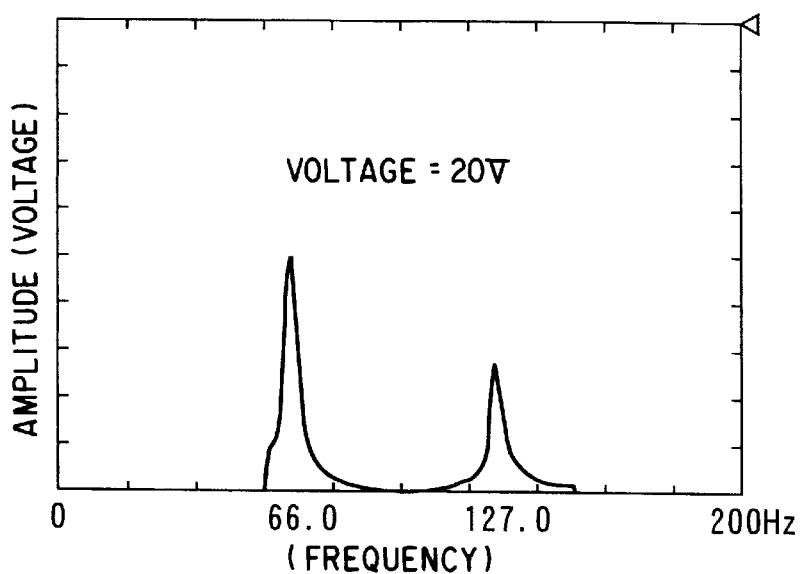
FIG. 3
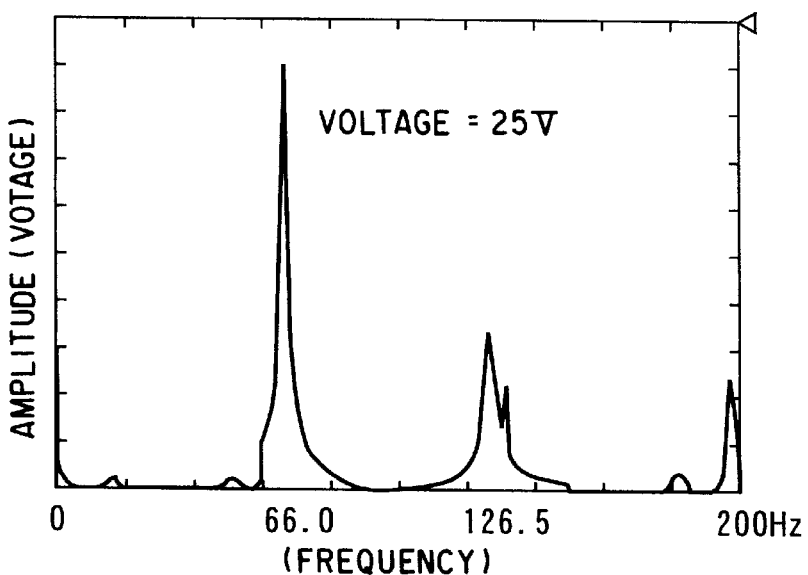
FIG. 4
| | 20V | 25V |
|---|---|---|
| 120Hz | 2.25mm | 2.96mm |
| 115Hz | 1.68mm | 2.16mm |
| 110Hz | 1.49mm | 1.94mm |
| 105Hz | 1.41mm | 1.84mm |
FIG. 5

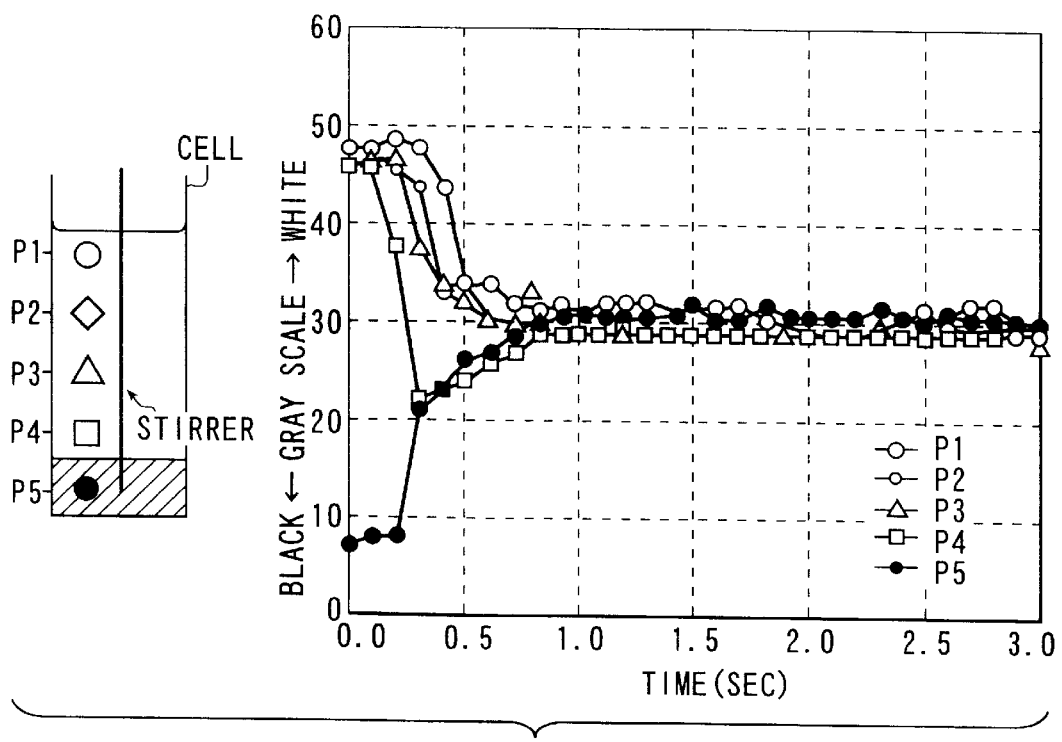
F I G. 7

STIRRING DEVICE AND AUTOMATIC ANALYZER INCORPORATING THE STIRRING DEVICE

BACKGROUND OF THE INVENTION

The present invention relates to a stirring device for use in inspection of samples in chemical and biochemical fields, which is designed to mix reagents, reaction liquids or the like and to stir the resultant mixture.

Stirrers, each having piezoelectric elements, are superior to rotary-type stirrers in terms of stirring efficiency. They therefore help to enhance the operating performance of automatic analyzers.

A conventional stirrer having piezoelectric elements will be described, with reference to FIGS. 2A, 2B and 2C. FIG. 2A is a front view, FIG. 2B is a rear view, and FIG. 2C is a side view.

This stirrer has a so-called "bimorph" structure. That is, it comprises a metal shim 201 and two piezoelectric ceramic elements 202 are attached to both surfaces of the shim 201. The metal shim 201 and the elements 202 constitute an actuator.

When an AC voltage is applied to the piezoelectric ceramic elements 202, the elements 202 are repeatedly expand and contract. The metal shim 201 is thereby vibrated. One end of the shim 201 is held in place by a screw 203. The other end of the shim 201 extends with the same material having a narrow portion, thus forming a blade 204. The blade 204 is inserted into a reaction cell and immersed in the liquid contained in the reaction cell. By the metal shim 201 is vibrated, the blade 204 is vibrated, so the liquid in the reaction cell is stirred. The weight of the screw 205 controls the vibration amplitude of the blade 204.

A cover 206 conceals all but the blade 204. Cover 206 protect the vibration of the piezoelectric ceramic element.

In recent years it has been demanded that automatic analyzers be made smaller and that two or more automatic analyzers be used in combination. To make an automatic analyzer, the reaction tubes in the reaction tank of the analyzer are arranged at a shorter distance.

An automatic analyzer may have two stirrers that are arranged side by side when they stir the liquid in two adjacent reaction tubes at the same time. To stir the liquid in the two adjacent reaction tubes, the stirrers need to be spaced for the same distance as the reaction tubes are spaced apart. If the stirrers are arranged very close to each other, their covers 206 may interfere with each other.

Therefore, reducing the distance between adjacent blades 204 has its limit, so the distance between the adjacent reaction cells is limited. Consequently, the automatic analyzer cannot be made as small as is demanded.

BRIEF SUMMARY OF THE INVENTION

The object of the present invention is to provide a stirring device which can be manufactured with high efficiency and which can help to miniaturize automatic analyzers.

According to the invention, there is provided a stirring device comprising: an actuator having a vibration element; a cover covering the actuator; a blade designed to be vibrated by the actuator; and connecting means connecting the blade to the actuator like the central axis of vibration amplitude of the blade is situated substantially along the side of the cover.

The blade is secured to the spacer, and the spacer is fastened to the actuator. Thus, if two stirring devices of the invention are simultaneously used to stir the liquids contained in two reaction cells, the distance between the blades of the stirrers can be shortened by the thickness of the spacer. This makes it possible to reduce the distance between the adjacent reaction cells arranged in the reaction tank of an automatic analyzer. Therefore, the stirring device according to this invention serves to miniaturize the automatic analyzer.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

FIG. 3 is a graph showing how the vibration amplitude of the blade changes as the frequency of the AC power supplied to the piezoelectric ceramic elements is changed, while the voltage of the AC power remains at 20V;

FIG. 4 is a graph depicting how the vibration amplitude of the blade changes as the frequency of the AC power supplied to the piezoelectric ceramic elements is changed, while the voltage of the AC power remains at 25V;

FIG. 5 is a table showing the amplitudes at which the blade of the stirrer vibrated at various frequencies, when different voltages were applied to the piezoelectric ceramic elements;

FIG. 7 is a graph showing the relation between the time for the stirrer of this invention is operated and the stirring degree which the stirrer of the invention achieves;

DETAILED DESCRIPTION OF THE INVENTION

An embodiment of the present invention will be described, with reference to the accompanying drawings.

Figure 1A:
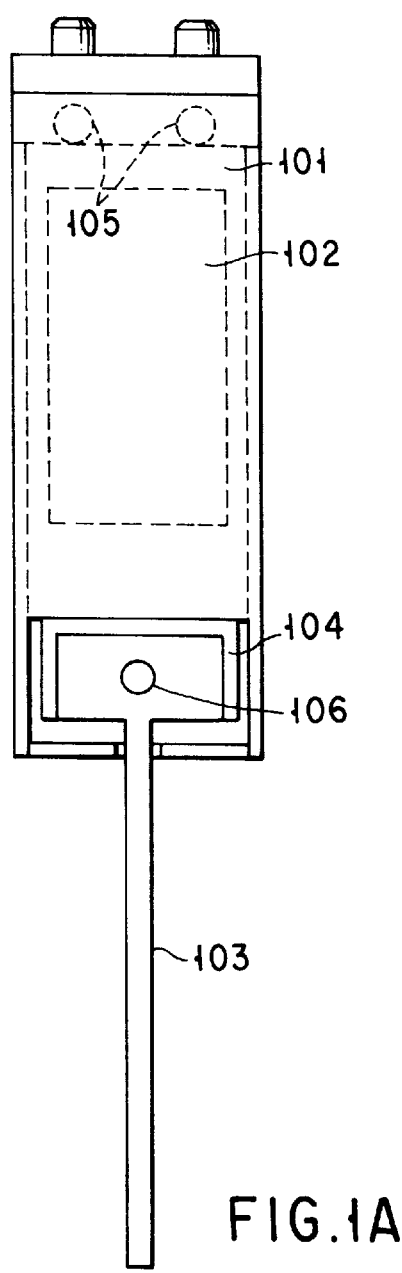
FIG. 1A is a front view of a stirrer according to the present invention.
Figure 1B:
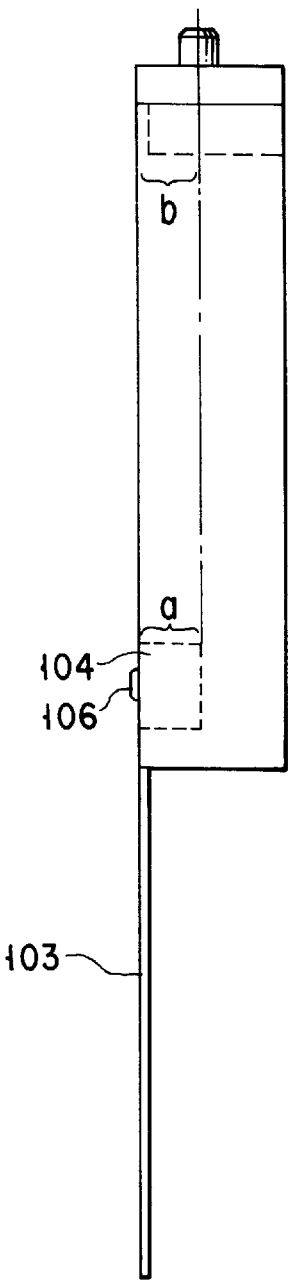
FIG. 1B is a side view of the stirrer according to the invention.
Figure 1C:
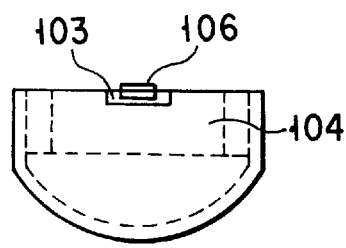
FIG. 1C is a bottom view of the stirrer according to the invention.

FIGS. 1A, 1B and 1C are schematic front, side and bottom views of a stirrer according to the invention. In FIGS. 1A, 1B and 1C, the broken lines indicate the components that cannot be seen from outside.

As shown in 1A, 1B and 1C, the stirrer comprises a metal shim 101 and the piezoelectric ceramic element 102. The piezoelectric element 102 may be attached to only one surface of the shim 201. In this case, stirrer has a unimorph structure. Alternatively, two piezoelectric ceramic elements 102 may be attached to both surfaces of the shim 201. If so, the stirrer has a bimorph structure. The metal shim 101 and the piezoelectric ceramic element or element 102 constitute an actuator.

When an AC voltage is applied from a power supply (not shown) to the piezoelectric ceramic elements 102, the elements 102 are repeatedly expand and contract. The metal shim 101 is thereby vibrated. One end of the shim 101 is firmly held in place by a screw 105 so that it may not vibrate by itself or may not be displaced. A blade 103, provided for stirring the liquid in a reaction cell, is connected to the other end of the shim 201 through a spacer 104. The blade 103, the spacer 104 and the shim 210 are fixed by a screw 106. The spacer 104 has a thickness of 10 mm and bellow. The vibration of the metal shim 101 is transmitted to the blade 103. The distal end of the blade 103 is thereby vibrated to stir the liquid in the reaction cell.

The blade 103 is made of the same material as the metal shim 101. The surfaces of the blade 103 are covered with a protective coating, so that the blade 103 may not be affected by various kind of liquids in the reaction cell.

The spacer 104 needs to be hard and heavy enough to enable the blade 103 to vibrate at its distal end at such amplitude as to stir thoroughly the liquid in the reaction cell. More specifically, it must be hard not to absorb the vibration of the metal shim 101. The amplitude at which the distal end of the blade 103 vibrates depends on the voltage and frequency of the AC power driving the piezoelectric ceramic elements 102 and the weights of the spacer 104 and screw 106. The spacer 104 has a thickness a which is greater than the thickness b defined by screws 105 that fasten the metal shim 101.

The inventors hereof conducted experiments to determine the values at which the voltage and frequency of the AC power for driving the elements 102 and the weights of the spacer 104 and screw 106 should be set in order to vibrate the blade 103 at secondary mode. The results were as is shown in FIGS. 3 and 4. Here, vibration of Nth mode means that N fixed points exist on the blade 103 which is vibrating. Since the blade 103 vibrates in the secondary mode, there is one fixed point other than the point where the screw 106 fastens the blade 103 to the shim 102. (For details, see Jpn. Pat. Appln. KOKAI Publication No. 4-363665, for example.)

The spacer 104 and the screw 106 used in the experiments had a total weight of 0.8 g.

FIG. 3 shows how the vibration amplitude of the blade 103 changes as the frequency of the AC power supplied to the piezoelectric ceramic elements 102 is changed from 0 Hz to 200 Hz, while the voltage of the AC power remains at 20V. The frequency is plotted on the abscissa, while the voltage converted from the vibration amplitude of the distal end of the blade 103 is plotted on the ordinate. The larger the amplitude, the higher the voltage which is generated.

As seen from FIG. 3, the vibration amplitude at the distal end of the blade 103 reached a peak when the frequency of the AC power was about 66.0 Hz, and reached another peak when the frequency of the AC power was about 127.0 Hz. The voltage at the second peak was about half the voltage at the first peak, or at the frequency of about 66.0 Hz. Namely, the blade 103 vibrated in the primary mode at the frequency of about 66.0 Hz and in the secondary mode at the frequency of about 127.0 Hz.

FIG. 4 shows how the voltage converted from the vibration amplitude of the blade 103 changes as the frequency of the AC power supplied to the piezoelectric ceramic elements 102 is changed from 0 Hz to 200 Hz, while the voltage of the AC power remains at 25V. As can be understood from FIG. 4, the distal end of the blade 103 vibrated in the primary mode when the frequency of the AC power was about 66.0 Hz as in the case where the voltage of the AC power remained at 20V, and in the secondary mode when the frequency of the AC power was about 126.5 Hz.

It is known that the blade 103 can stir a reaction liquid to render the same homogeneous within a shorter time when it vibrates in the secondary mode than when it vibrates in the primary mode, as is disclosed in, for example, Jpn. Pat. Appln. KOKAI Publication No. 4-363665.

The inventors applied AC powers of 20V and 25V, each at various frequencies (i.e., 120 Hz, 115 Hz, 110 Hz and 105 Hz), vibrating the piezoelectric ceramic elements 102 to vibrate the blade 103 in the primary mode. And they measured the amplitudes at which the distal end of the blade 103 vibrated in the primary mode. The results were as is shown in FIG. 5.

Reaction cells have a width of about 4 to 5 mm. The amplitude at which the distal end of the blade 103 vibrates must therefore be 3 mm or less. FIG. 5 shows that the distal end of the blade 103 vibrated in secondary mode at an amplitude of 3 mm or less when the piezoelectric ceramic elements 102 were supplied with AC power of a frequency ranging from 105 Hz to 120 Hz and a voltage of 20V or 25V, furthermore the spacer 104 and the screw 105 had a total weight of 0.8 g.

Figures 2A, 2B, 2C:
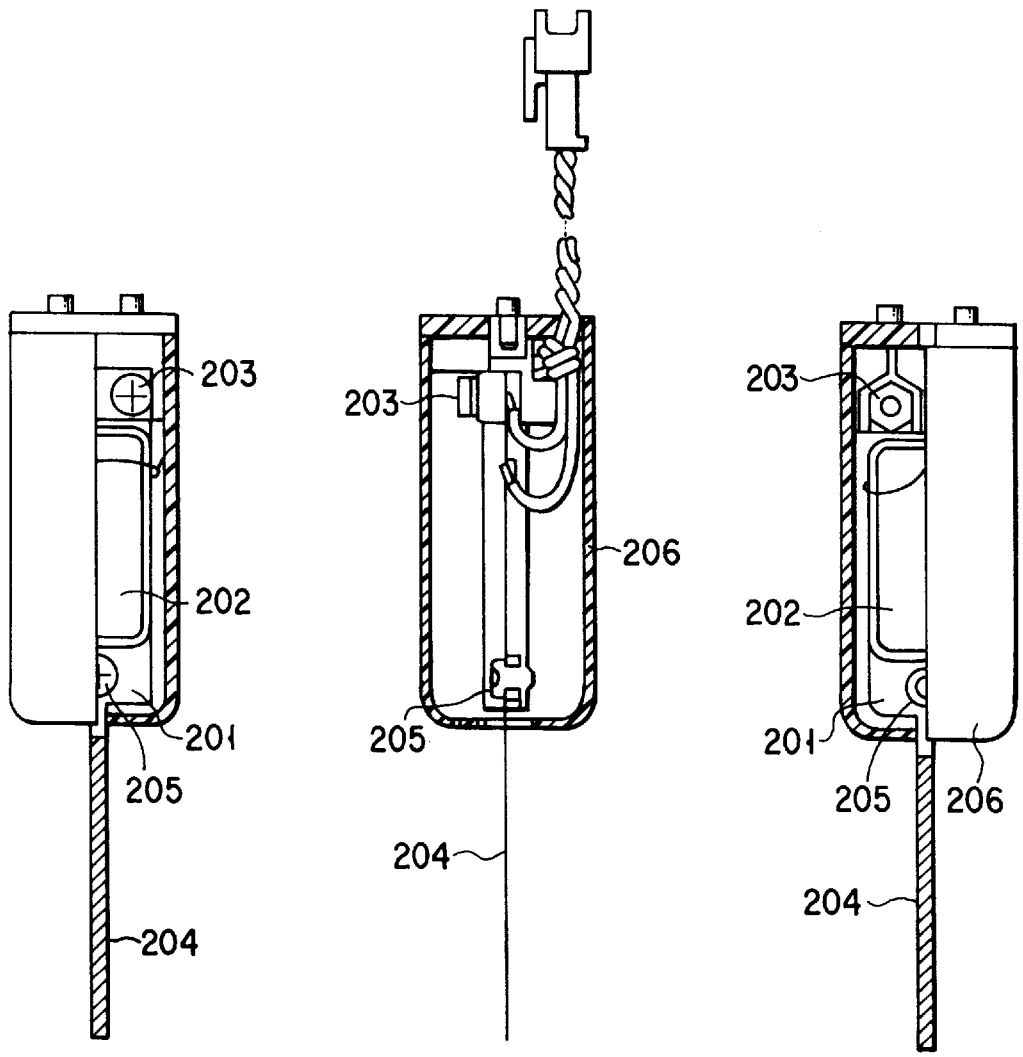
FIG. 2A is a front view of a conventional stirrer.
FIG. 2B is a side view of the conventional stirrer.
FIG. 2C is a rear view of the conventional stirrer.

Further, the inventors operated the conventional stirrer shown in FIGS. 2A to 2C, wherein the screw 205 has a weight of 0.8 g, by supplying AC power having a voltage of 25V and a frequency of 120 Hz to the piezoelectric ceramic elements 202, thereby stirring the liquids in a reaction cell. And they measured the time required to stir the liquid in each reaction cell thoroughly. The results are shown in FIG. 6.

Figure 6:
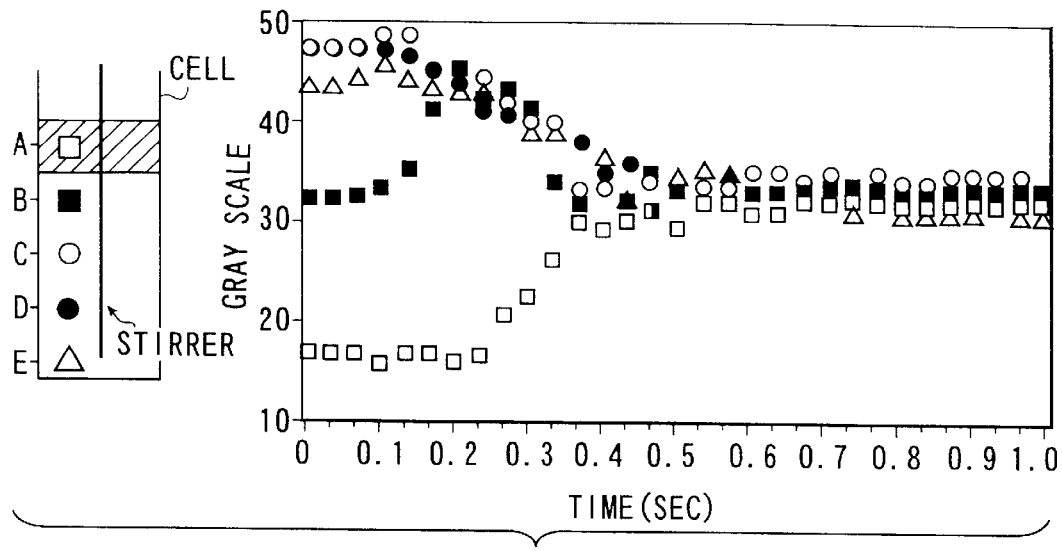
FIG. 6 is a graph illustrating the relation between the time for the conventional stirrer is operated and the stirring degree, which the conventional stirrer achieves.

More specifically, saline solution was poured into the reaction cell and dye liquid (Evans blue) was then poured thereinto, thus forming two layers of liquids as is illustrated in the left part of FIG. 6. Then, chromaticity was measured at five levels A to E in the reaction cell, at different times as the saline solution and the dye liquid were stirred by the conventional stirrer. The chromaticities thus measured plotted, obtaining the graph shown in the right part of FIG. 6. In this graph, the chromaticity is plotted on the ordinate, and the stirring time on the abscissa. The greater the value of the ordinate, the higher the transparency of the liquids.

As seen from FIG. 6, the chomaticities at levels A to E, which differed before the stirring of the saline solution and dye liquid, approached an average value as the stirring proceeded. When the chromaticities changed to the average value, the saline solution and the dye liquid were mixed completely. As can be understood from FIG. 6, it took about 0.6 to 0.7 seconds until the chromaticities measured at levels A to E changed to the average value, in the case of the conventional stirrer.

The inventors operated the stirrer according to the invention (FIGS. 1A–1C), wherein the spacer 104 and the screw 106 have a total weight of 0.8 g, by supplying the same AC power AC power to the piezoelectric ceramic elements 102 as was supplied to the elements 202 of the conventional stirrer (FIGS. 2A–2C). More precisely, saline solution was poured into the reaction cell and dye liquid (Evans blue) was then poured thereinto, thus forming two layers of liquids as is illustrated in the left part of FIG. 7. Then, chromaticity was measured at five levels A to E in the reaction cell, at different times as the saline solution and the dye liquid were stirred by the stirrer of the present invention. The chromaticities thus measured plotted, obtaining the graph shown in the right part of FIG. 7.

As is evident from FIG. 7, it took about 0.8 to 0.9 seconds until the chromaticities measured at levels A to E changed to the average value, in the case of the stirrer according to the present invention. The time required to stir the saline solution and dye liquid completely is almost the same as the time the conventional stirrer required to stir the solution and liquid thoroughly. This means that stirring efficiency is much the same the stirrer of the invention as the conventional stirrer.

An automatic analyzer incorporating stirrers according to the invention will be described, with reference to FIG. 8. The automatic analyzer comprises a reaction tank, a plurality of reaction cells arranged side by side in the reaction tank, and a plurality of stirring units, and a plurality of drive units. Each stirring unit has one stirrer of the type shown in FIGS. 1A–1C. Each drive unit is designed to drive one stirrer vertically so that the blade of the stirrer may move into and out of the liquid contained in a reaction cell.

Figure 8:
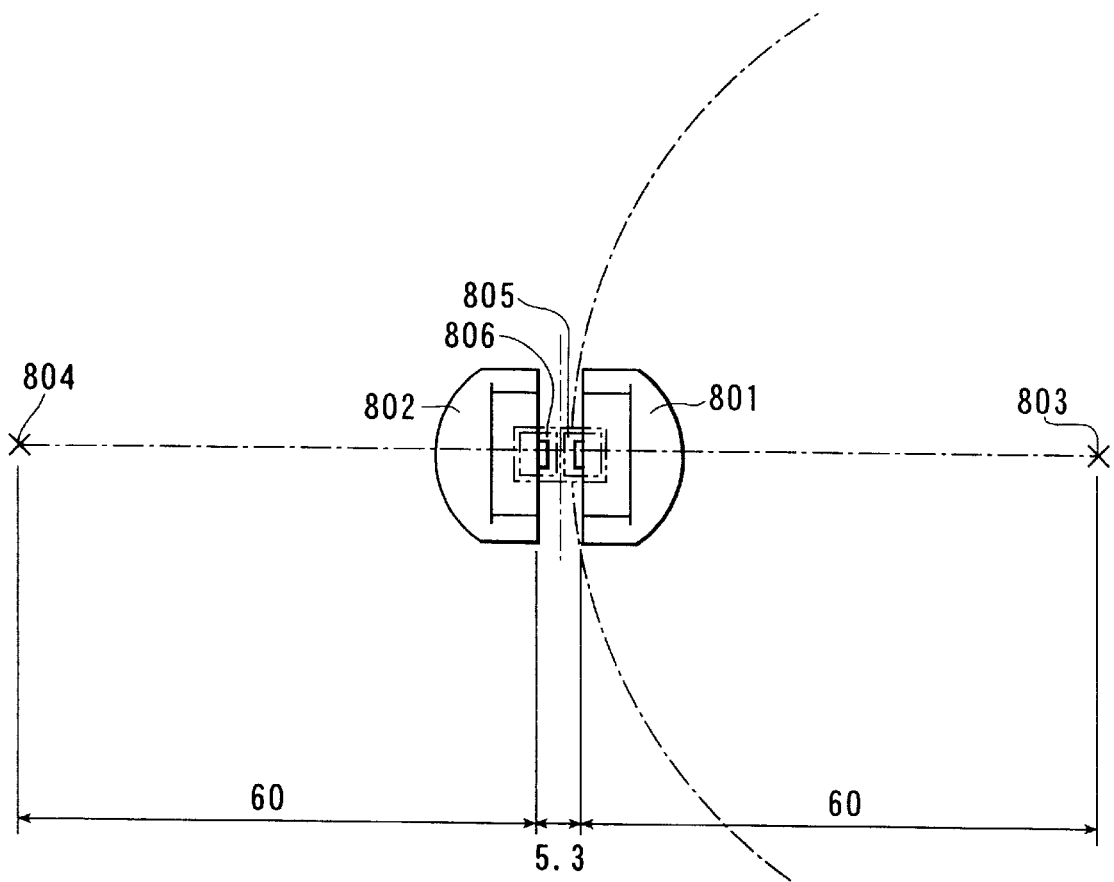
FIG. 8 is a plan view of an automatic analyzer in which the stirrer of the invention is stirring the liquid in two adjacent reaction cells.

FIG. 8 is a plan view of the automatic analyzer. As shown in FIG. 8, the automatic analyzer comprises two drive units (not shown), two stirring units 801 and 802, two shafts 803 and 804, and two reaction cells 805 and 806. The reaction cells 805 and 806 are arranged side by side, each containing liquid. The stirring units 801 and 802 can be turned on the shafts 803 and 804, respectively, and can stir the liquids in the reaction cells 805 and 806 at the same time.

In operation, the drive units (not shown) rotate the shafts 803 and 804, whereby the stirring units 801 and 802 are turned on the shafts 803 and 804, respectively. When the stirring units 801 and 802 move to the reaction cells 805 and 805, the drive units stop rotating the shafts 803 and 804. The stirring units 801 and 802 are thereby located right above these cells 805 and 806, respectively. Then, the drive units lower the shafts 803 and 804. As a result, the blade of the stirring unit 801 is thereby inserted into the reaction cell 805, and the blade of the stirring unit 802 is inserted into the reaction cell 806. Next, an AC voltage is applied to the piezoelectric elements of both stirring units 801 and 802, vibrating the blades of the units 801 and 802. The stirring units 801 and 802 therefore start stirring the liquids in the reaction cells 805 and 806 at the same time.

When the liquids in the reaction cells 805 and 806 are stirred completely (or upon lapse of a preset stirring time), the application of AC voltage to the stirring units 801 and 802 is stopped. Thus, the blade of the units 801 and 802 stop vibrating. Then, the drive units (not shown) lift the shafts 803 and 804 simultaneously, thereby moving the stirring units 801 and 802 upward. The blades of the units 801 and 802 are thereby pulled up from the reaction cells 805 and 806. Thereafter, the drive units rotate the shafts 803 and 804, thus returning the stirring units 801 and 802 to their respective initial positions.

Figure 9:
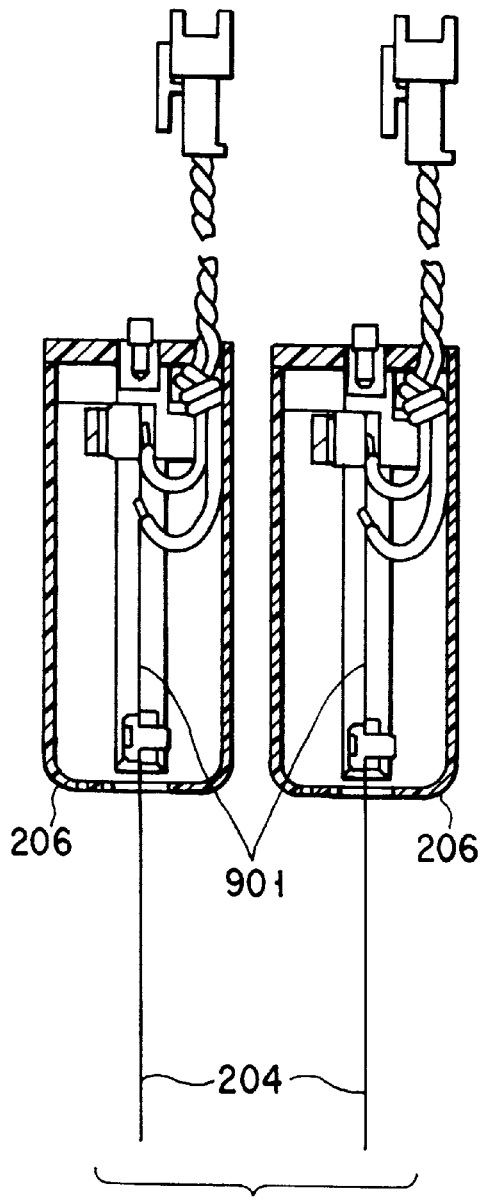
FIG. 9 is a diagram showing two conventional stirrer arranged side by side, above two adjacent reaction cells.

FIG. 9 shows two identical stirrers of the conventional type (FIGS. 2A–2C) arranged side by side when they stir the liquids in the reaction cells arranged side by side at the same time. The blade 204 of each stirrer extends downward from the lower end of the actuator 901, passing through the center hole made in the bottom of the cover 206 which is a substantially rectangular box. Once the covers 206 of these stirrers touch each other, the blades 204 can no longer approach each other. The shortest possible distance between the blades 204 is 20 mm. It follow that the distance between the center of the reaction cells needs 20 mm or more.

As indicated above, the blade 204 of either conventional stirrer is made integral with the metal shim 101. Inevitably, the step of bonding the piezoelectric ceramic elements 202 to the metal shim 201 and the step of applying a coating to the surfaces of the blade 204 to protect the blade 204 against various kinds of liquids cannot be performed simultaneously; they must be sequentially conducted in the order mentioned.

Figure 10:
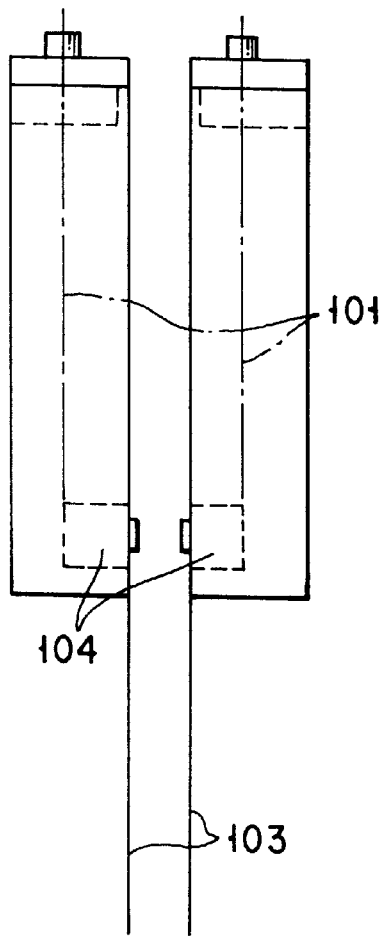
FIG. 10 is a diagram showing two stirrer of the present invention, arranged side by side above two adjacent reaction cells.

FIG. 10 shows two identical stirrers according to the invention (FIGS. 2A–2C) arranged side by side when they stir the liquids in the reaction cells arranged side by side at the same time. The blade 103 of each stirrer is secured at the end of the actuator 101 through the spacer 104 by a screw 106. Therefore, the central axis of vibration amplitude of the blade 103 (i.e., the stirring section) is situated substantially along the side of the cover which covers the actuator 101 having two piezoelectric ceramic elements and which allows the actuator 101 to vibrate freely.

Since the blade 103 of each stirrer extends in a plane close and parallel to the side of the cover, two stirrers can be arranged as shown in FIG. 10, with their blades 103 located far closer to each other than is possible with the conventional stirrers arranged as shown in FIG. 9. Hence, in the automatic analyzer shown in FIG. 8, incorporating two stirrers of this invention, the distance between the reaction cells 805 and 806 can be reduced to about 5.3 mm. This helps to make the reaction tank, and ultimately to miniaturize the automatic analyzer.

As FIGS. 1A–1C show, the metal shim 101 and the blade 103 are not formed integral. In other words, the shim 101 and the blade 103 are separate components. Hence, the step of bonding the piezoelectric ceramic elements 102 to the metal shim 101 and the step of applying a protective coating to the surfaces of the blade 103 can be performed at the same time. Hence, the stirrer according to the present invention can be manufactured with high efficiency and at high yield.

In the stirrer of this invention, the blade is secured to the spacer, which is fastened to the actuator. If two stirrers of the invention are simultaneously used to stir the liquids contained in two reaction cells, the distance between the blades of the stirrers can be shortened by the thickness of the spacer. This makes it possible to reduce the distance between the adjacent reaction cells arranged in the reaction tank of an automatic analyzer. The stirrer according to the present invention, therefore, serves to miniaturize the automatic analyzer.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An automatic analyzer comprising:
 a reaction tank configured to hold a plurality of reaction cells arranged side by side; and a plurality of stirring units, each including, an actuator with a shape of a plate and designed to vibrate;

a cover covering the actuator and configured to protect a vibration of the actuator;

a blade configured to stir liquids contained in the reaction cells;

a connecting device configured to connect the blade to the actuator such that the vibration of the actuator is transmitted to the blade and a distance between covers of any adjacent stirring units is substantially equal to a distance between blades on the adjacent stirring units while the liquids are being stirred in the reaction cells, and a drive unit configured to position the stirring units above the reaction cells so as to immerse the blades in the liquids contained in the reaction cells.

2. The automatic analyzer according to claim 1, wherein said actuator has a unimorph structure and comprises a flexible shim and one piezoelectric ceramic element bonded to one surface of the flexible shim.

3. The automatic analyzer according to claim 1 and wherein said actuator has a bimorph structure and comprises a flexible shim and two piezoelectric ceramic elements bonded to both surfaces of the flexible shim.

4. The automatic analyzer according to claim 1, wherein said connecting device comprises a spacer which is hard enough to transmit the vibration of the actuator to the blade.

5. The automatic analyzer according to claim 1, further comprising a power supply configured to apply an AC voltage of a specific frequency to the actuator, thereby to vibrate the blade in Nth mode.

6. The automatic analyzer according to claim 4, wherein said spacer has a thickness of at most 10 mm.

7. The automatic analyzer according to claim 4, wherein said spacer has a weight such that a vibration amplitude at a distal end of the blade falls within a prescribed range.

8. An automatic analyzer comprising:

a reaction tank configured to hold a plurality of reaction cells arranged side by side; and a plurality of stirring units, each including, an actuator with a shape of a plate and designed to vibrate, a cover covering the actuator and configured to protect a vibration of the actuator, a blade configured to stir liquids contained in the reaction cells, a connecting device configured to connect the blade to the actuator such that the vibration of the actuator is transmitted to the blade and a distance between covers of any adjacent stirring units is equal to or shorter than a distance between blades on the adjacent stirring units while the liquids are being stirred in the reaction cells, and a drive unit configured to position the stirring units above the reaction cells so as to immerse the blades in the liquids contained in the reaction cells.

9. The automatic analyzer according to claim 8, wherein said actuator has a unimorph structure and comprises a flexible shim and one piezoelectric ceramic element bonded to one surface of the flexible shim.

10. The automatic analyzer according to claim 8, wherein said actuator has a bimorph structure and comprises a flexible shim and two piezoelectric ceramic elements bonded to both surfaces of the flexible shim.

11. The automatic analyzer according to claim 8, wherein said connecting device comprises a spacer hard enough to transmit the vibration of the actuator to the blade.

12. The automatic analyzer according to claim 8, further comprising:

a power supply configured to apply an AC voltage of a specific frequency to the actuator, thereby to vibrate the blade in an Nth mode.

13. The automatic analyzer according to claim 11, wherein said spacer has a thickness of at most 10 mm.

14. The automatic analyzer according to claim 11, wherein said spacer has a weight such that a vibration amplitude at a distal end of the blade falls within a prescribed range.

15. An automatic analyzer comprising:

a reaction tank configured to hold a plurality of reaction cells arranged side by side; and a plurality of stirring units, each including, an actuator with a shape of a plate and designed to vibrate, a cover covering the actuator and configured to protect a vibration of the actuator, a blade configured to stir liquids contained in the reaction cells, a connecting device configured to connect the blade to the actuator such that the vibration of the actuator is transmitted to the blade and a distance between covers of any adjacent stirring units is substantially equal to a distance between central vibration axes of blades on the adjacent stirring units while the liquids are being stirred in the reaction cells, and a drive unit configured to position the stirring units above the reaction cells so as to immerse the blades in the liquids contained in the reaction cells.

16. An automatic analyzer comprising:

a reaction tank configured to hold a plurality of reaction cells arranged side by side; and a plurality of stirring units, each including, an actuator with a shape of a plate and designed to vibrate, a cover covering the actuator and configured to protect a vibration of the actuator, a blade configured to stir liquids contained in the reaction cells, a connecting device configured to connect the blade to the actuator such that the vibration of the actuator is transmitted to the blade and a distance between covers of any adjacent stirring units is substantially equal to or shorter than a distance between central vibration axes of blades on the adjacent stirring units while the liquids are being stirred in the reaction cells, and a drive unit configured to position the stirring units above the reaction cells so as to immerse the blades in the liquids contained in the reaction cells.

* * * * *